United States Patent [19]

Berry et al.

[11] Patent Number: 5,278,064

[45] Date of Patent: Jan. 11, 1994

[54] *AMYCOLATOPSIS MEDITERRANEI* STRAINS USEFUL TO PREPARE A87689 COMPOUNDS

[75] Inventors: Dennis R. Berry, Greenwood; Anne H. Dantzig, Crawfordsville; Manuel Debono, Indianapolis; Robert Hamill, Greenwood; R. Michael Molloy, Danville; Raymond C. Yao, Carmel, all of Ind.

[73] Assignee: Eli Lilly and Company, Indianapolis, Ind.

[21] Appl. No.: 878,254

[22] Filed: May 4, 1992

Related U.S. Application Data

[63] Continuation-in-part of Ser. No. 738,969, Aug. 1, 1991, abandoned.

[51] Int. Cl.$^5$ .................. A61K 35/00; C12R 1/01; C12P 1/04
[52] U.S. Cl. .................. 435/252.1; 424/122; 435/195; 435/253.2; 435/253.5
[58] Field of Search ............ 424/122; 435/145, 252.1, 435/253.2, 253.5

[56] References Cited

FOREIGN PATENT DOCUMENTS

0405864AZ 1/1991 European Pat. Off. ... C07D 493/10
0407939   1/1991 European Pat. Off. ........ C12P 1/06

OTHER PUBLICATIONS

Kusumi, T., et al., The Structures of Quartromicins A1, A2, A3: Novel Macrocyclic Antiviral Antibiotics Possessing Four Tetronic Acid Moieties, *J. Am. Chem. Soc.*, 113:8947–8948 (1991).

A. Fredenhagen, G. Fendrich, F. Märki, J. Gruner, F. Raschdorf, and H. Peter, "Duramycins B and C, Two New Lanthionine Containing Antibiotics as Inhibitors of Phospholipase A2," *J. Antibiotics* 43: 1403–1412 (1990).

K. Nakagawa and A. Torikata, "Microbial Conversion of Milbemycins: 30-Oxidation of Milbemycin A$_4$ and related Compounds by *Amycolatopsis autotrophica* and *Amycolatopsis mediterranei*" *J. Antibiotics* 43: 1321–1328 (1990).

*Primary Examiner*—Herbert J. Lilling
*Attorney, Agent, or Firm*—Steven A. Fontana; Leroy Whitaker

[57] ABSTRACT

Fermentation product A87689 is produced by a strain of *Amycolatopsis mediterranei* selected from NRRL 18815 and NRRL 18851, or an A87689-producing mutant thereof. A87689, its $C_{1-6}$-alkyl ether and $C_{1-6}$-alkanoyl ester derivatives and pharmaceutically acceptable salts thereof are phospholipase A$_2$ inhibitors that are useful as antiinflammatory agents. Fermentation products known as BU-3889V, its components and pharmaceutically acceptable salts thereof, are phospholipase A$_2$ inhibitors that are also useful as antiinflammatory agents.

3 Claims, 6 Drawing Sheets

AMYCOLATOPSIS MEDITERRANEI STRAINS USEFUL TO PREPARE A87689 COMPOUNDS

CROSS-REFERENCE TO RELATED APPLICATION

This application is a continuation-in-part of application Ser. No. 07/738,969, filed Aug. 1, 1991, and now abandoned.

TECHNICAL FIELD OF THE INVENTION

The present invention relates to the isolation and characterization of a microbially-synthesized compound, its derivatives and pharmaceutically acceptable salts thereof, and processes for enzyme inhibition. More particularly, this invention includes a novel phospholipase $A_2$ ($PLA_2$) inhibitor, A87689, isolated in substantially pure form from fermentation cultures of *Amycolatopsis mediterranei*. This invention also relates to pharmaceutical compositions containing the compounds, and the method of use of the present compounds for inhibiting $PLA_2$ and treating certain inflammatory indications in animals. This invention further relates to a process for inhibiting phospholipase $A_2$ in animals using previously known BU-3889V components.

BACKGROUND OF THE INVENTION

Inflammatory disorders account for a significant amount of debilitating diseases. Inflammatory states, such as arthritis, psoriasis, asthma, and possibly atherosclerosis, stem from inflammatory reactions in the joints, skin, and blood vessels. It is generally believed that a central role in the inflammatory reaction is the production of phospholipid metabolites called eicosanoids. The eicosanoids represent a family of important mediators such as the leukotrienes, prostaglandins, lipoxins, hydroxyeicosatetranoic acid, and thromboxanes. It is believed that the generation of eicosanoids is dependent on the availability of arachidonic acid which is liberated from phospholipids by the action of phospholipase $A_2$ ($PLA_2$).

$PLA_2$ is the common name for phosphatide 2-acylhydrolase, which catalyzes the hydrolysis of the sn-2-acyl ester bond of phosphoglycerides which results in the production of equimolar amounts of lysophospholipids and free fatty acids [Dennis, E. A., *The Enzymes*, Vol. 16, Academic Press, New York, (1983)]. $PLA_2$ enzymes are found in all living species and form a diverse family of enzymes. Over forty $PLA_2$ enzymes have been structurally characterized, and they show a high degree of sequence homology. [J. Chang, J. H. Musser, and H. McGregor, "Phospholipase $A_2$: Function and Pharmacological Regulation," *Biochem. Pharm.* 36: 2429-2436, (1987)].

The best characterized varieties of $PLA_2$ enzyme are the secreted forms, which are released into the extracellular environment where they aid in the digestion of biological materials. The secreted forms have a mw of about 12-15,000 (Chang, et al, supra). In contrast, cytosolic $PLA_2$s are found in small amounts within the cell and play a key role in the biosynthetic pathway leading to the formation of the platelet activating factors and the eicosanoids. [Mobilio, D. and Marshall, L. A., "Recent Advances in the Design and Evaluation of Inhibitors of Phospholipase $A_2$," *Ann. Reports in Med. Chem.* 24; 157-166, (1989)]. The cytosolic $PLA_2$s have a mw of approximately 85,000. [Clark, J. D., Lin, L. L., Kriz, W., Ramesha, C. S., Sultzman, Lin, A. Y., Merlona, N., Knots, J. L., *Cell* 65: 1043-1051 (1991)]. Free arachidonic acid is the rate limiting precursor for the production of eicosanoids and is liberated from its membrane phospholipid store by the action of cytosolic $PLA_2$. [Dennis, E. A., "Phospholipase $A_2$ Mechanism: Inhibition and Role in Arachidonic Acid Release," *Drug Dev. Res.* 10: 205-220, (1987)]. The same enzymatic step also produces lysophospholipids which may be converted to form platelet-activating factors. Thus, it is believed that cytosolic $PLA_2$ is central to the regulation of the biosynthetic pathways of potent lipid mediators of inflammation.

Due to the central role in the inflammation process that is played by cytosolic $PLA_2$, it is desirable to identify and characterize new inhibitors of the enzyme. Such inhibitors may lead to new therapies for the treatment of arthritis, asthma, atherosclerosis, and inflammatory diseases of the skin (e.g. psoriasis) and the bowel (e.g. irritable bowel syndrome). Identification of such specific $PLA_2$ inhibitors may aid the medical community in reaching the goal of control of inflammatory disease states.

THE PRIOR ART

Several $PLA_2$ inhibitors have been described, but A87689 differs from those compounds. For instance, duramycins B and C have been identified as $PLA_2$ inhibitors by Fredenhagen et al. [A. Fredenhagen, G. Fendrich, F. Märki, J. Gruner, F. Raschdorf, and H. Peter, "Duramycins B and C, Two New Lanthionine Containing Antibiotics as Inhibitors of Phospholipase $A_2$," *J. Antibiotics* 43: 1403-1412 (1990)]. The duramycins differ from A87689 because they contain sulfur, whereas A87689 does not. Another phosphlipase $A_2$ inhibitor is cinatrin A, which differs from A87689 in size (Eur. Pat. no. 405864-A.) The cinatrins have a molecular weight (mw) of less than 500, whereas A87689 has a mw of 1184.

The species of microorganism which synthesizes A87689 is a new strain of the species *Amycolatopsis mediterranei*. Other strains of *A. mediterranei* have been known to make useful compounds. For instance, one strain of *A. mediterranei* has been shown to modify the antibiotic milbemycin $A_4$ to one or more new products, such as 30-hydroxymilbemycin $A_4$ and 26,30-dihydroxymilbemycin $A_4$ [K. Nakagawa and A. Torikata, "Microbial Conversion of Milbemycins: 30-Oxidation of Milbemycin $A_4$ and related Compounds by *Amycolatopsis autotrophica* and *Amycolatopsis mediterranei*," *J. Antibiotics* 43: 1321-1322 (1990)]. The milbemycins are antimicrobial in nature, whereas A87689 lacks antimicrobial activity.

Another microorganism, fermentation culture *Amycolatopsis orientalis* ATCC 53884, biosynthetically produces complex BU-3889V and its bioactive components $A_1$, $A_2$, $A_3$, $D_1$, $D_2$ and $D_3$. European Patent Publication 0.407,939. The method of use for the BU-3889V complex in the art has been limited to antiviral activity, whereas the present invention relates to the use of the BU-3889V complex, the compounds of the complex also known as quartromicins, for $PLA_2$ inhibition.

One should note that the name of the A87689-producing microbial species was changed in 1986, when two new genera were split from the nocardioform actinomycetes. The new genus Amycolata and the new genus Amycolatopsis were identified at that time by Lechevalier et al. [M. P. Lechevalier, H. Prauser, D. P. Labeda, J. Ruan, "Two New Genera of Nocardioform actinomycetes Amycolata New-Genus and Amycolatopsis New-Genus," *Int. J. Syst. Bacteriol.* 36: 29–37 (1986)].

SUMMARY OF THE INVENTION

This invention relates to a fermentation product, A87689, and to its $C_{1-6}$-alkyl ether and $C_{1-6}$-alkanoyl ester derivatives and salts. These forms of A87689 are collectively referred to as an A87689 compound or A87689 compounds throughout this specification. The invention also relates to a process for producing A87689 by culturing a new strain of the microorganism *Amycolatopsis mediterranei*, selected from *A. mediterranei* NRRL 18815 or NRRL 18851, or an A87689-producing mutant thereof, under submerged fermentation conditions. A87689 and its derivatives, and pharmaceutically acceptable salts thereof, are useful for the control of inflammation, particularly in asthmatic individuals, arthritic individuals, and psoriatic individuals. Thus, methods and compositions for administering this compound for these purposes are also part of this invention.

This invention also relates to biologically-purified cultures selected from the *Amycolatopsis mediterranei* strains NRRL 18815 or NRRL 18851, or an A87689-producing mutant of NRRL 18815 or NRRL 18851. The purified cultures are useful for producing the $PLA_2$-inhibitor A87689.

This invention further relates to the use of complex BU-3889V, including its bioactive components $A_1$, $A_2$, $A_3$, $D_1$, $D_2$, and $D_3$, its derivatives and pharmaceutically acceptable salts thereof, for inhibiting $PLA_2$ and for the control of inflammation particularly in asthmatic, arthritic and psoriatic individuals.

DESCRIPTION OF THE DRAWINGS

The infrared (IR) absorption spectra of A87689 and exemplery salts and derivatives (in KBr pellet) are shown in FIGS. 1-5 as follows.

DETAILED DESCRIPTION OF THE INVENTION

This invention relates to a new fermentation product which has been designated "A87689". A87689, which is useful as an enzyme inhibitor, is generally purified from the culture medium in the form of an alkaline earth metal salt, such as the calcium salt. Further aspects of this invention are processes for producing A87689 by culturing a novel strain of the microorganism *Amycolatopsis mediterranei* selected from NRRL 18815 and NRRL 18851, or an A87689-producing mutant thereof, and biologically purified cultures of the *Amycolatopsis mediterranei* strains which produce it. As those skilled in fermentation processes will recognize, although the compound is generally isolated from the microorganism in alkaline earth salt form, other forms of the compound may then be generated by derivatization in the laboratory, as described infra.

In discussions of utility, the form of compound administered will be referred to, such as the "calcium salt of A87689" or the "free acid of A87689"; or if one or more than one of the derivatives is being discussed, it may be referred to as the "A87689 compound or compounds."

The calcium salt of A87689 is a white, crystalline material which has the following characteristics:
Molecular weight: 1222.418
Empirical formula: $C_{66}H_{70}O_{20}Ca$
FAB-MS(M+1): Found: 1223.4175; Calculated: 1223.4254
Solubility: Very slightly soluble in water (1 mg/mL) at pH 7; quite soluble in aqueous solution of pH 12.0 or greater; soluble in DMSO at 4 mg/mL; slightly soluble in methanol; insoluble in organic solvents such as EtOAc, acetone, diethyl ether, hydrocarbons, chloroform, higher alcohols.

Figure 1:
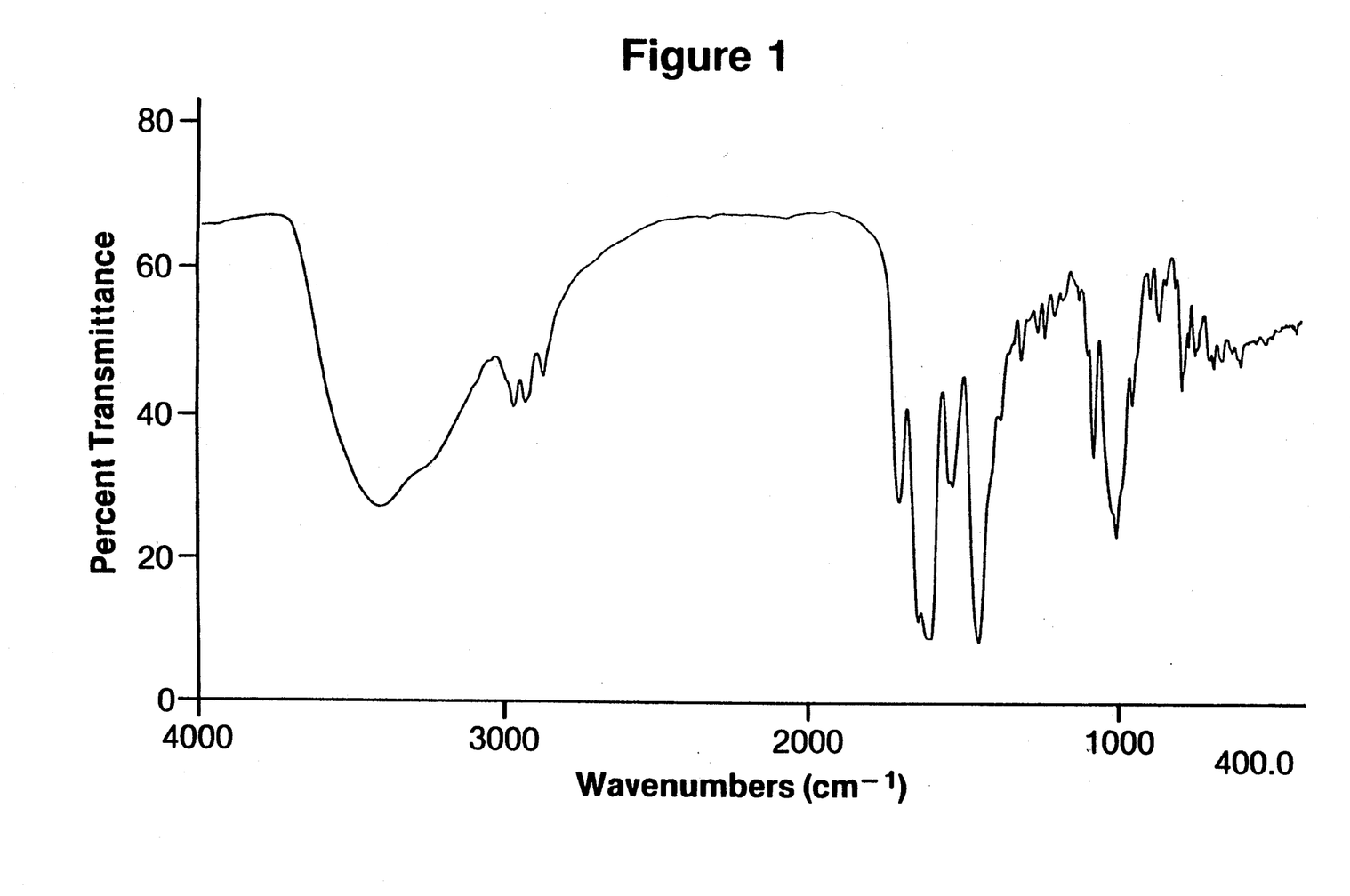
FIG. 1—A87689 calcium salt.

The IR spectrum of the calcium salt of A87689 (KBr pellet) is shown in FIG. 1 of the accompanying drawings. The most significant absorption maxima occur at the following frequencies ($cm^{-1}$): 3402, 1711, 1609, 1534, 1449, 1078, 1006 and 792.

A87689 is capable of forming salts and has at least four hydroxyl groups which can be esterified or form ether derivatives. Thus, the $C_{1-6}$-alkanoyl ester and $C_{1-6}$-alkyl ether derivatives and the salts of A87689 and of these derivatives (A87689 compounds) are also part of this invention. The tetra-acetate and the tetramethyl ether derivatives, as free acids and salts, are examples. The A87689 compounds are useful as agents which reduce inflammation. The pharmaceutically-acceptable salts are particularly useful.

Such salt forms, including hydrates thereof, are frequently crystalline and therefore useful for forming solutions or formulating pharmaceutical compositions. Pharmaceutically acceptable salts with bases include those formed from the alkali metals, alkaline earth metals, non-toxic metals, ammonium, and mono-, di- and tri-substituted amines. Examples of such salts include sodium, potassium, lithium, calcium, magnesium, aluminum, zinc, ammonium, trimethylammonium, triethanolammonium, pyridinium, substituted pyridinium and like salts.

The pharmaceutically acceptable acid addition salts used in this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caparate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluen-sulfonate, chlorobenzenesulfonate, eylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts.

For purposes of discussion of taxonomy, the *A. mediterranei* cultures NRRL 18815 and NRRL 18851 will be called A87689 and A87689.1, respectively. Culture A87689 was isolated from a soil mixture (dilution). Derivative strain A87689.1 was produced by chemical mutagenesis. The novel compound made by the A87689 and A87689.1 cultures will be called "A87689".

This invention also relates, therefore, to a biologically purified culture of the microorganism *Amycolatopsis mediterranei* selected from NRRL 18815 or NRRL 18851, or an A87689-producing mutant thereof. These microorganisms are useful because they produce the PLA$_2$-inhibitor A87689.

Cultures A87689 and A87689.1 have been deposited and made part of the stock culture collection of the Midwest Area Northern Regional Research Center, Agricultural Research Service, United States Department of Agriculture, 1815 North University Street, Peoria, Ill., 61604, from which they are available to the public under the following accession numbers: NRRL 18815 and NRRL 18851.

Taxonomic studies of cultures A87689 and A87689.1 were carried out by Frederick P. Mertz of the Lilly Research Laboratories. Based on these studies, the microorganisms A87689 and A87689.1 are classified as new members of the species *Amycolatopsis mediterranei*. This classification is based on direct laboratory comparisons and examination of published descriptions of similar species.

Methods Used

The methods followed were those recommended by the International Streptomyces Project (ISP) for the characterization of Streptomyces species [Shirling, E. B. and Gottlieb, D., "Methods for characterization of Streptomyces species," *Int. J. Syst. Bacteriol.* 16: 313-340, (1966)] and those recommended for the characterization of Nocardia species [Gordon, R. E., Barnett, D. A., Handerhan, J. E., and Pang, C. H., "*Nocardia coeliaca, Nocardia autotrophica*, and the Nocardin Strain," *Int. J. Syst. Bacteriol.* 24(1): 54-63 (1974).] ISCC-NBS Centroid Color Charts, standard sample No. 2106, were used to assign color names to the reverse side and to aerial hyphae (National Bureau of Standard, 1958, U.S. Department of Commerce, Washington, D.C.)

Morphology was studied using an optical light microscope and a scanning electron microscope (SEM). The isomer of diaminopimelic acid (DAP) and the carbohydrates in hydrolysates of whole cells were established by the chromatographic methods of Becker et al. [Becker, B., Lechevalier, M. P., Gordon, R. E. and Lechevalier, H. E., "Rapid Differentiation between Nocardia and Streptomyces by Paper Chromatography of Whole-cell Hydrolysates," *Appl. Microbiol.* 12,421-423 (1964)] and of Lechevalier and Lechevalier [Lechevalier, M. P. and Lechevalier, H., in *A University Laboratory Approach*, Dietz and Thayer (eds.), Society for Industrial Microbiology Special Publication No. 6, Arlington, Va., pp. 227-233.]

Phospholipids were determined by the procedure of Lechevalier et al. [Lechevalier, M. P., Stern, A. E. and Lechevalier, H. A., "Phospholipids in the taxonomy of Actinomycetes," in *Actinomycetes*, Schaal and Pulverer (eds.), Zbl. Bakt. Suppl. 11 Gustav Fischer Verlag, (1981)].

Menaquinone composition was determined by following the procedures of R. M. Kroppenstedt [in *Chemical Methods in Bacterial Systematics*, M. Goodfellow and D. E. Minnikin (eds.), 1985, pp. 173-196] and M. D. Collins [ibid., pp. 267-285]. Fatty acid analysis was done using the HP 5898A Microbial Identification System of Miller and Berger [Miller, L. and Berger, T., "Bacterial Identification by Gas Chromatography of Whole Cell Fatty Acids," Hewlett-Packard Application Note 228-41, 8 pp. (1985)].

Fatty acid methyl esters were made from lyophilized whole cells grown under identical conditions. Mycolic acids were determined by the methods proposed by Minnikin [Minnikin, D. E., Hutchinson, I. G., and Caldicott, A. B., "Thin-Layer Chromatography of Methanolysates of Mycolic Acid-Containing Bacteria," *J. Chromatography* 188: 221-233 (1980)].

Cultural Characteristics

Culture A87689 grew well on complex and defined media. Culture A87689 did not produce aerial hyphae except for trace amounts of white aerial hyphae on ISP medium 4. The reverse side had a distinctive orange pigmentation. On ISP medium 2 produced a faint light brown soluble pigment which was released into the medium. Table 1 summarizes these cultural characteristics.

TABLE 1

Cultural Characteristics of A87689[1]

| Medium | Growth | Reverse Color | Aerial Growth | Soluble Pigment |
|---|---|---|---|---|
| ISP medium 2 | Abundant | 50. s.O | None | L. Brown |
| ISP medium 3 | None | | | None |
| ISP medium 4[2] | Abundant | 50. s.O | Trace | None |
| ISP medium 5 | None | | | None |
| ISP medium 7 | Poor | 90. gy.Y | None | None |
| ATCC No. 172 | Good | 50. s.O | None | None |
| BENNETTS | Fair | 53. m.O | None | None |
| Calcium-malate | Abundant | 48. V.O | None | None |
| CZAPEKS | Abundant | 50. s.O | None | None |
| TPO[3] | Abundant | 71. m.OY | None | None |

[1]Incubated at 30° C. for 28 days
[2]Mycelium color 263. White
[3]Tomato Paste Oatmeal Agar

Morphological Characteristics

Culture A87689 exhibited no fragmentation. The hyphae segment into long strands of conidia arranged in typical cobweb morphology characteristic of nonstreptomycete actinomycetes. The conidia are cylindrical in shape, have a smooth surface, and average 1.4×0.4 µm. Sporangia or motile cells are not present.

Physiological Characteristics

Culture A87689 produced acid from the following carbohydrates: adonitol, D-arabinose, L-arabinose, cellobiose, D-galactose, D-fructose, D-glucose, glycerol, glycogen, i-inositol, inulin, lactose, D-maltose, mannitol, D-mannose, melebiose, raffinose, L-rhamnose, D-ribose, sucrose, trehalose, and D-xylose.

A87689 did not produce acid from cellulose, dextrin, dulcitol, ethanol, i-erythritol, D-melezitose, methyl-D-glucoside, salicin, sorbitol, L-sorbose and xylitol.

Culture A87689 utilized the following carbohydrates with ISP medium 9 as the basal medium: L-arabinose, D-fructose, D-galactose, D-glucose, inositol, D-mannitol, D-raffinose, L-rhamnose, salicin, sucrose, and D-xylose. Culture A87689 utilized sodium salts of the following organic acids (as sole sources of carbon for energy and growth): acetate, butyrate, citrate, formate, lactate, malate, mucate, oxalate, propionate, pyruvate, and succinate. Culture A87689 was unable to utilize benzoate and tartrate. A87689 decomposed casein, hypoxanthine and L-tyrosine. It was unable to hydrolyze adenine and xanthine. A87689 produced esculinase, gelatinase, H$_2$S, phsophatase and urease. It did not produce melanoid pigments. A87689 grew between 15° C. and 42° C. A87689 tolerated up to 4% NaCl. The culture is sensitive to lysozyme.

Cell-Wall Analysis

Hydrolyzed whole cells contained mesodiaminopimelic acid (DAP). Diagnostic sugars in the whole cell extracts were arabinose and galactose. Phospholipids present were phosphatidyl ethanolamine (PE), phosphatidyl inositol (PI), and diphosphatidyl glycerol (DPG). A87689 has a type IV cell wall composition and a type A whole-cell sugar pattern [Lechevalier, M. P. and Lechevalier, H., "Chemical composition as a criterion in the classification of aerobic actinomycetes," Int. J. Syst. Bacteriol. 20: 435–443] and a type PII phospholipid pattern [Lechevalier, M. P., Stern, A. E., Lechevalier, H. A., "Phospholipids in the Taxonomy of Actinomycetes," in Actinomycetes, Schaal and Pulverer (eds.) Zbl. Bakt. Suppl. II Gustav Fischer Verlag, Stuttgart, New York]. Mycolic acids were not present in whole cell hydrolysates. The major menaquinones detected were MK-9 (H$_4$), plus minor amounts of MK-8 (H$_4$), MK-9 (H$_6$), and MK-10 (H$_4$).

Identity of A87689

Culture A87689 is a non-streptomycete strain with a type IV cell wall, type A whole cell sugar pattern, type PII phospholipid pattern, and no mycolates. These chemotaxonomic characteristics plus its cultural and morphological properties place A87689 in the genus Amycolatopsis. There are six species and one subspecies in this genus: A. azurea, A. fastidiosa, A. mediterranei, A. orientalis, A. orientalis subsp. lurida, A., rugosa, and A. sulphurea. When compared to these existing strains, culture A87689 was most similar to A. mediterranei. Culturally, it was almost identical. The morphological characteristics were minimal due to the absence of aerial hyphae, but its primary growth was identical to A. mediterranei. The biochemical characteristics of A87689 and A. mediterranei are also almost identical. Table 2 reports the differences between A87689 and A. mediterranei.

TABLE 2

Differential characteristics of A87689 and *Amycolatopsis mediterrannei.*

| Characteristic | A87689 | A. mediterranei |
|---|---|---|
| Decomposition of: | | |
| L-Tyrosine | + | − |
| Resistant to: | | |
| 4% NaCl | + | − |
| Growth at: | | |
| 42° C. | + | − |
| Acid produced from: | | |
| Adonitol | + | − |
| Inulin | + | − |

Figure 6:
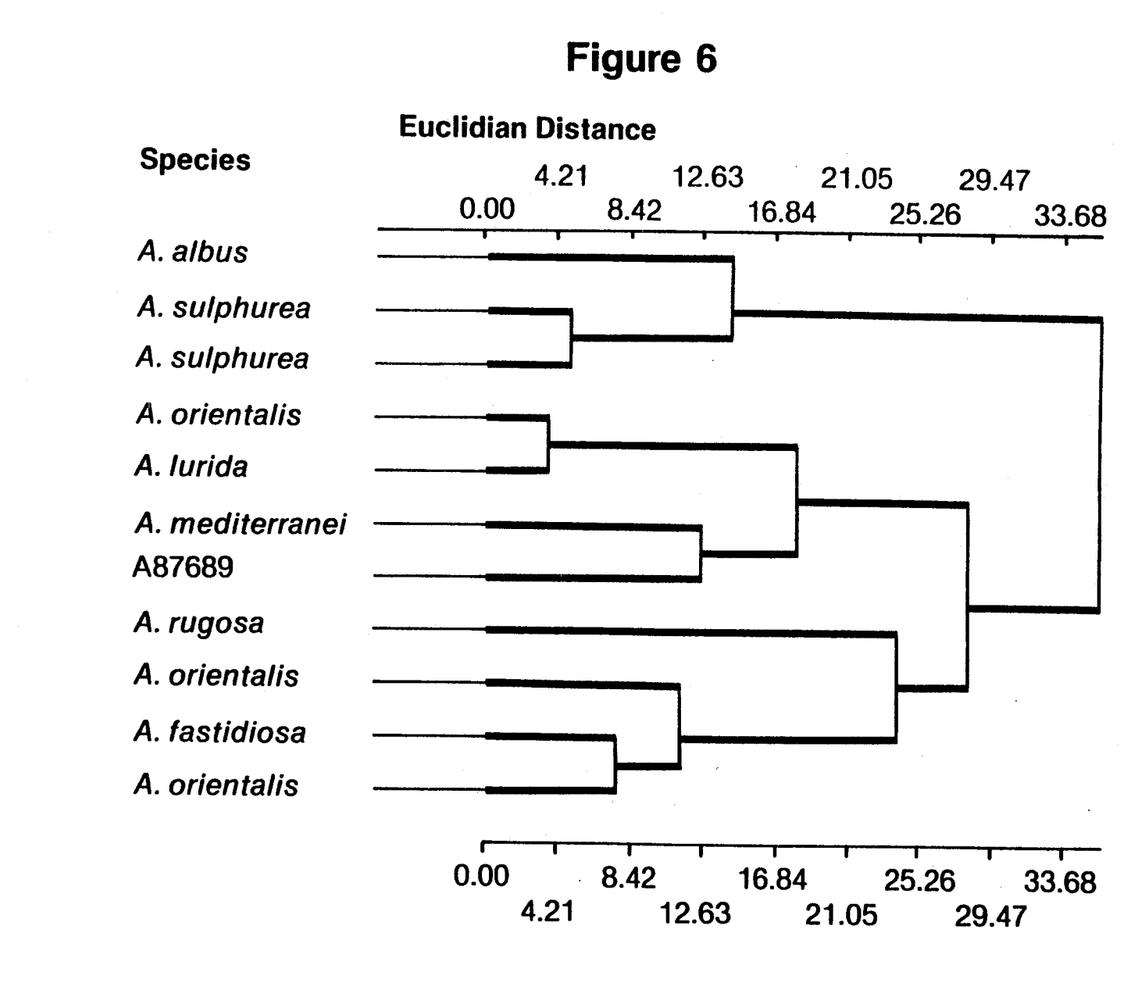
FIG. 6 is a computer-generated dendrogram constructed from fatty acid profiles.

Fatty acid analysis was done on A87689 and all the available Amycolatopsis strains. Table 3 presents a comparison of the percentage fatty acids. A computer-generated dendrogram constructed from fatty acid profiles is presented in FIG. 6. This dendrogram shows the relationship of A87689 to the other Amycolatopsis species measured by Euclidean distance. Cultures showing relatedness below the level of 10.00 are interpreted as being synonymous, that is, the same species. A87689 is related to A. mediterranei at the level of 12.00.

Principal component analysis is a branch of multivariate statistics that deals with internal relationships of a set of variables. In this analysis the greatest amount of variance within the original data or test results is expressed as principal components [Alderson, G. "The application and relevance of non hierarchic methods in bacterial taxonomy," in Computer-assisted bacterial systematics, Goodfellow, M., Jones, D., and Priest, F. G. (eds.) Academic Press, New York (1985)]. Thus, a plot showing scatter or variability can be constructed. Relationships can then be evaluated by examining this variance, and a microbial population can be characterized. A two-dimensional principal component plot based on fatty acids was constructed and showed culture A87689 clustering with A. mediterranei. Although there is variation between A87689 and A. mediterranei, this variation is a strain and not a species difference. Therefore, culture A87689 is classified as a strain of Amycolatopsis mediterranei. [Lechevalier, M. P., Hauser, H., Labeda, D. P., Ruan, J. S., "Two new genera of nocardioform actionomycetes: Amycolata gen. nov. and Amycolatopsis gen. nov.," Int. J. Syst. Bacteriol. 36: 21–37.

TABLE 3

Percentage fatty acid composition of A87689 and Amycolatopsis species.

| Fatty Acid | A87689 | A. orientalis | A. lurida | A. fastidiosa | A. rugosa | A. mediterranei | A. sulphurea |
|---|---|---|---|---|---|---|---|
| 14:0 Iso | 2.29 | 6.36 | 5.68 | 5.56 | 0.98 | 2.35 | 2.64 |
| 15:0 Iso | 7.90 | 9.98 | 9.32 | 10.76 | 2.23 | 15.51 | 17.66 |
| 15:0 Anteiso | 1.03 | 1.69 | 1.53 | 0.70 | — | 2.36 | 6.14 |
| 15:1 B[1] | 2.09 | — | — | 3.12 | 4.44 | 1.89 | — |
| 15:0 | 4.58 | 6.25 | 6.37 | 2.82 | 0.54 | 4.65 | 5.51 |
| 16:1 Iso H | 5.19 | 0.45 | 1.00 | 12.76 | 31.39 | 4.21 | — |
| 16:0 Iso | 37.10 | 21.46 | 24.20 | 39.71 | 29.80 | 29.32 | 13.24 |
| 16:0 Anteiso | 0.21 | — | — | 0.23 | — | 1.23 | 0.53 |
| 15:0 Iso2OH | — | 7.64 | 6.50 | — | — | — | 17.25 |
| 16:1 Cis 9 | 2.74 | — | — | 0.82 | 4.55 | 1.18 | — |
| 16:0 | 0.93 | 1.58 | 1.10 | 0.37 | 0.27 | 0.65 | 8.29 |
| 17:1 Iso G | 1.55 | 0.32 | 0.56 | — | — | 1.76 | — |
| 17:0 Iso | 0.65 | 0.57 | 0.51 | 1.02 | 0.68 | 1.02 | 2.74 |
| 17:0 Anteiso | 1.45 | 0.88 | 0.85 | 1.05 | 0.57 | 4.29 | 6.71 |
| 17:1 B | 15.65 | 18.75 | 18.61 | 1.89 | 3.32 | 12.37 | 1.70 |
| 17:1 C | 7.19 | 12.99 | 13.50 | 15.64 | 19.19 | 4.28 | 7.23 |
| 17.0 | 1.79 | 8.56 | 6.84 | 0.72 | 0.17 | 3.02 | 8.92 |
| 18:1 Iso F | 5.95 | 1.15 | 2.45 | — | 0.20 | 8.15 | — |

[1]B, C, F, G, and H, indicate double bond positions/configurations that are unknown.

Comparison of Derivative Strains

The A87689.1 strain is sufficiently similar macroscopically to the A87689 strain to be classified as a strain of *Amycolatopsis mediterranei*. The two strains differ in the amount of A87689 they produce. The A87689.1 strain produces approximately two-fold more A87689 compound than the A87689 strain produces.

A87689 is produced by culturing an A87689-producing strain of *Amycolatopsis mediterranei* under submerged aerobic conditions in a suitable culture medium until a recoverable amount of A87689 is produced. A87689 can be recovered using various isolation and purification procedures understood in the art.

The culture medium used to grow the *Amycolatopsis mediterranei* cultures can be any one of a number of media. For economy in production, optimal yield, and ease of product isolation, however, certain culture media are preferred. Thus, for example, preferred carbon sources in large-scale fermentation are glucose and maltose, although ribose, xylose, fructose, galactose, mannose, mannitol, soluble starch, potato dextrin, methyl oleate, oils such as soybean oil and the like can also be used.

Preferred nitrogen sources are cottonseed flour, peptionized milk and digested soybean meal, although fish meal, corn steep liquor, yeast extract, enzyme-hydrolyzed casein, beef extract, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism.

For preferred production of substantial quantities of A87689, submerged aerobic fermentation in stirred bioreactors is preferred. Small quantities of A87689 may be obtained by shake-flask culture. Because of the time-lag in production commonly associated with inoculation of large bioreactors with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger bioreactor. The vegetative inoculum medium can be the same as that used for larger fermentations, but other media are also suitable.

A87689 compound is produced by the A87689-producing organisms when grown at temperatures between about 27° and about 32° C. Optimum temperatures for A87689 production appear to be about 30° C.

As is customary in submerged aerobic culture processes, sterile air is blown into the vessel from the bottom while the medium is stirred with conventional turbine impellors. In general, the aeration rate and agitation rate should be sufficient to maintain a level of dissolved oxygen of at least 45% of air saturation with an internal vessel pressure of 5 atmospheres.

Production of the A87689 compound can be followed during the fermentation by testing extracts of the broth for $PLA_2$ activity. The snake venom (*Naja naja*) $PLA_2$ assay system described infra is a useful assay for this purpose.

Following its production under submerged aerobic fermentation conditions, the A87689 compound can be recovered from the fermentation medium by methods used in the art. The A98689 produced during fermentation of the A87689-producing organism occurs mainly in the broth.

A87689 can be recovered from the biomass by a variety of techniques. A preferred technique involves filtering whole fermentation broth with a filter aid such as diatomaceous earth. The filtrate thus obtained is then adsorbed onto a high porous polymer adsorbent of the polystyrene type, such aa DIAION HP-20 (Mitsubishi Chemical Industries, Ltd., Tokyo) or AMBERLITE XAD-2 or AMBERLITE XAD-4 (Rohm and Haas, Philadelphia, Pa.). The adsorbent is washed with water and eluted with an organic-aqueous solution, such as methanol-water. The eluate is lyophilized and concentrated. In a preferred separation procedure, the lyophilized material is dissolved in dimethyl sulfoxide (DMSO) and chromatographed on a reverse-phase silica gel adsorbent ($C_8$ or $C_{18}$). Fractions are eluted in organic-aqueous buffer, such as acetonitrile:ammonium acetate.

Phospholipase A2 Inhibitory Activity

The compounds of this invention are useful for the reduction of inflammation of tissues because they inhibit $PLA_2$, an enzyme that is involved in the regulation of tissue inflammation.

The A87689 compounds have shown inhibitory activity in a number of assays which specifically detect $PLA_2$ activity. More specifically, the compounds were active in an in vitro assay utilizing isolated snake venom (*Naja naja*) $PLA_2$, an in vitro assay utilizing purified human cytosolic $PLA_2$, and a whole cell in vitro assay which detects the inhibition of secretion of metabolites of phospholipids (leukotriene and thromboxane).

Significantly, the claimed compounds were not active when tested in a 5-lipoxygenase assay, revealing their specificity for $PLA_2$.

In addition, the compounds have shown activity in in vivo assays for anti-inflammatory activity. Specifically, the compounds were active in three adjuvant-induced arthritis models.

Two salt forms of A87689 were tested in the biological assays. One form was soluble in both water and DMSO. This is the sodium salt of A87689. The other form was insoluble in water, but soluble in DMSO. This is the calcium salt of A87689. The latter form was tested either as a solution in DMSO or as a suspension in 1% carboxymethyl-cellulose (CMC).

In addition, the activity of derivatives and salts of A87689 were compared in one of the biological assays, the snake venom (*Naja naja*) $PLA_2$ assay.

Thus, the present invention is also directed to a method for reducing inflammation in animals which comprises administering to an animal an inflammation-inhibiting amount of an A87689 compound.

One preferred embodiment of the invention is a method for reducing the swelling which occurs in arthritic animals, which comprises administering to the animal an amount of A87689 compound sufficient to reduce the swelling.

In another preferred embodiment, the invention is directed to a method for treating asthma, which comprises administering to an animal an amount of A87689 compound sufficient to reduce the inflammation of the respiratory system that occurs in asthmatic animals.

In yet another embodiment, this invention provides a method for treating psoriasis, which comprises administering to an animal suffering from psoriasis an amount of A87689 compound that is effective to reduce the psoriatic lesions.

As previously mentioned, fermentation culture *Amycolatopsis orientalis* ATCC 53884 biosynthetically produces complex BU-3889V which includes its bioreactive components $A_1$, $A_2$, $A_3$, $D_1$, $D_2$ and $D_3$. The taxonomic description of *A. orientalis* ATCC 53884, and the processes for producing and isolating the bioactive components, are known in the art (see, European Patent Publication 0,407,939). Each of these components have been found only to be effective for the inhibition of certain viruses including herpes simplex virus, human immunodeficiency virus (HIV) and influenza.

This invention features a novel utility for these components wherein $PLA_2$ activity in animals should be inhibited and which, consequently, should regulate tissue inflammation in such animals.

In particular, this invention includes a method for inhibiting $PLA_2$ activity in animals which comprises administering to said animal a $PLA_2$-inhibiting amount of at least one compound selected from the group consisting of BU-3889V $A_1$, BU-3889V $A_2$, BU-3889V $A_3$, BU-3889V $D_1$, BU-3889V $D_2$, BU-3889V $D_3$ or a pharmaceutically acceptable salt thereof.

Furthermore, the BU-3889V components should reduce inflammation in animals, assist in the treatment of arthritic disease in animals, and also treat asthma. Thus, one preferred embodiment of the invention includes a method of reducing inflammation in animals which comprises administering to said animal an inflammation inhibiting amount of at least one compound selected from the group consisting of BU-3889V $A_1$, BU-3889V $A_2$, BU-3889V $A_3$, BU-3889V $D_1$, BU-3889V $D_2$, BU-3889V $D_3$, or a pharmaceutically acceptable salt thereof.

This invention features another preferred embodiment which includes a method of treating arthritic disease in animals which comprises administering to said animal an effective amount of at least one compound selected from the group consisting of BU-3889V $A_1$, BU-3889V $A_2$, BU-3889V $A_3$, BU-3889V $D_1$, BU-3889V $D_2$, BU-3889 V $D_3$, or a pharmaceutically acceptable salt thereof.

In an additional preferred embodiment, the invention is directed to a method of treating asthma which comprises administering to an animal an amount of at least one compound selected from the group consisting of BU-3889V $A_1$, BU-3889V $A_2$, BU-3889V $A_3$, BU-3889V $D_1$, BU-3889V $D_2$, BU-3889V $D_3$, or a pharmaceutically acceptable salt thereof, sufficient to reduce the inflammation of an asthmatic animal's respiratory system.

The BU-3889V components might also provide a method of treating psoriasis which comprises administering to an animal suffering from psoriasis at least one compound selected from the group consisting of BU-3889V $A_1$, BU-3889V $A_2$, BU-3889V $A_3$, BU-3889V $D_1$, BU-3889V $D_2$, BU-3889V $D_3$, or a pharmaceutically acceptable salt thereof.

As used above and throughout this specification, the term "effective amount" means that dosage of active compound sufficient to provide therapeutical treatment of the specified medical indication.

The term "active compound", as used throughout this specification, refers to at least one compound selected from A87689 or its derivatives, and BU-3889V components $A_1$, $A_2A_3$, $D_1$, $D_2$, and $D_3$, or the pharmaceutically acceptable salts thereof.

For therapeutic treatment of the specified indications, active compounds of this invention may be administered as such, or they can be compounded and formulated into pharmaceutical compositions in unit dosage form for parenteral, intravenous or transdermal administration or, preferably, oral administration. Such pharmaceutical compositions are prepared in a manner well known in the art and comprise at least one active compound associated with a pharmaceutically acceptable carrier. In such a composition, the active compound(s) are known as active ingredients. In making the compositions, the active ingredient(s) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders. Some examples of suitable carriers, excipients, and diluents include lactose, dextrose, sucrose, sorbitol, mannitol, starches, gum acacia, calcium phosphate, alginates, calcium salicylate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art. For oral administration active compounds can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects and other mammals, each unit containing a predetermined quantity of active compound calculated to produce the desired therapeutic effect, in association with the required pharmaceutical carrier.

The active compounds of this invention are effective over a wide dosage range. For example, daily dosages will normally fall within the range of about 0.1 mg/kg to about 50 mg/kg of body weight. In the treatment of adult humans, the dosage range from about 5 mg/kg to about 25 mg/kg, in single or divided doses, is preferred. However, it will be understood that the amount of the compound actually administered will be determined by a physician in light of the relevant circumstances including the relative severity of a particular malady, the choice of compound or compounds to be administered, the age, weight, and response of the individual patient, and the chosen route of administration. Therefore, the above dosage ranges are not intended to limit the scope of this invention in any way.

A87689 in In Vitro Phospholipase A2 Models

In Vitro Snake Venom (*Naja naja*) Assay

In this assay, endogenous phospholipases produced by the microorganisms are removed from the broth by filtration through a membrane filter (mw cut-off of 10,000, Centricon). Broth (100 μL) is incubated in a reaction mixture of a total volume of 0.540 mL for one hour at 37° C. The reaction mixture consists of 0.24 mM 1-palmitoyl-2-[6-[(7-nitro-2-1,3-benzoxadiazol-4-yl)amino]caproyl]phosphatidylcholine (PLA$_2$ chromogenic substrate, Avanti, Polar-Lipids, Inc., Alabaster, Ala.), 0.76 mM phosphatidyl choline, 10 mM TRITON X-100 (surfactant, Sigma), 10 mM CaCl$_2$, 37 mM TRIS-HCl at pH 8.5 (Sigma), 0.07 units/mL *Naja naja* PLA$_2$ (Sigma). The reaction is stopped by adding 0.2 mL of 0.25M ethylene diamine tetraacetate (EDTA). The product, 7-nitro-2-1,3-benzoxadiazol-4-yl]amino]caproic acid, is separated from the substrate by high performance liquid chromatography (HPLC). The assay mixture (20 μL) is injected onto a C$_8$ column (0.46×15 cm, ZORBAX) with a C$_8$ guard cartridge [Solvent, acetonitrile:water:acetic acid (40:60:1); Flow rate: 1.5 mL/min.; Detection of product: UV at 453 nm. Retention time: 3.72–3.76 minutes]. Tables 4 and 5 show the effect of A87689 compounds in this assay.

Human Cytosolic PLA$_2$ Assay

Cytosolic PLA$_2$ purified from human monoblast U937 cells was used to test the inhibitory activity of A87689 in vitro. The assay was performed as described in Kramer et al. [Kramer, R. M., Roberts, E. F. Manetta, J., and Putnam, J. E., "The Ca++-sensitive Cytosolic Phospholipase A$_2$ Is a 100-kD Protein in Human Monoblast U937 Cells," *J. Biol. Chem.* 266(8): 5268–5272]. Briefly, 50 μL of sonicated liposomes containing 1-palmitoyl-2-[$^{14}$C] arachidonoyl-sn-glycero-3-phosphocholine and 1,2-dioleoyl glycerol (2:1 molar ratio) are added to varying micromolar concentrations of test compound in 150 μL of assay buffer. This assay mixture contains 1 mM CaCl$_2$, 2 mM 2-mercaptoethanol, 150 mM NaCl, 50 mM N-[2-hydroxyethyl]piperazine-N$^1$-[2-ethane sulfonic acid] (HEPES) pH 7.5 and 1 mg/mL bovine serum albumin (BSA). To each tube, the enzyme (5 μL, diluted to yield 10–20% hydrolysis of the substrate) is added and the mixture is incubated at 37° C. for 15 min. The reaction is stopped with Doles reagent [Zhang, Y. Y., Deems, R. A., and Dennis, E. A. in *Methods in Enzymology*, vol. 197, p. 457, Academic Press, New York (1991)]. The free arachidonic label is extracted with heptane:water (1.2:1). The upper phase is removed to tubes containing 0.1 g silica gel, mixed, centrifuged at 1500×g and the supernatant is removed for scintillation counting. The degree of inhibition is calculated and graphed for each drug concentration, and expressed as the amount that inhibits the maximum reaction by 50% (IC$_{50}$.) The effect of A87689 in this assay is presented in Table 4. In this assay, the A87689 compounds were much more potent than were the classic inhibitors of venom or pancreatic PLA$_2$s, such as para-bromophenacyl bromide, mepacrine or manoalide.

Whole Cell PLA$_2$ Test

Human promyelocytic leukemia cells (HL-60), induced to differentiate into granulocyte-like cells by growth in the presence of 1.5% DMSO, release the leukotriene B$_4$ (LTB$_4$) and the thromboxane B$_2$ (TXB$_2$) in response to stimulation with the calcium ionophore A23187. The release of those eicosanoids is inhibited by treatment of the cells with the PLA$_2$ inhibitor manoalogue ([E, E]-2-[3-(2,5-dihydro-2-hydroxy-5-oxo-3-furanyl)propylidene]-6,10-dimethyl-5,9-undecadienal). Manoalogue is an inhibitor of a secreted form of PLA$_2$, (Reynolds, et al.) and an intracellular form of PLA$_2$ (Dennis, et al.). [Reynolds, et al. *J. American Chemical Society* 110: 5172, (1988); Dennis, et al. *J. Biol. Chem.* 264: 8520, (1989).]

The protocol for the HL-60 cell assay is as follows: HL-60 cells obtained from American Type Culture Collection (ATCC) are grown in suspension culture in RPMI 1640 medium (Gibco) supplemented with 10% fetal bovine serum, in a humidified atmosphere of 5% CO$_2$ at 37° C. Cells are induced to differentiate into granulocyte-like cells by culture in the presence of 1.5% DMSO for 7 days. Cells are harvested by centrifugation at 4° C. for 5 minutes and washed once in 118 mM NaCl, 4.6 mM KCl, 24.9 mM NaHCO$_3$, 1 mM KH$_2$PO$_4$ and 11.1 mM D-glucose, 5 mM HEPES, pH 7.4, supplemented with 0.1% BSA, 1.1 mM MgCl$_2$ and 1 mM CaCl$_2$. Washed cells are resuspended to a concentration of 1×10$^6$ cells/mL and prewarmed to 37° C. for 5 minutes prior to initiation of the assay. Cells are preincubated for 5 minutes with inhibitors, followed by a 5 minute incubation with a calcium ionophore, A23187. Reactions are terminated by centrifugation. Supernatants are decanted and processed for the enzyme immunoassays (EIAs). Enzyme immunoassays for leukotriene B$_4$ and thromboxane B$_2$ are performed in a final volume of 150 μL containing 100 mM potassium phosphate buffer, pH 7.4, 0.4 NaCl, 1 mM EDTA, 1.5 mM NaN$_3$ and 0.1% BSA with 5 μL sample for LTB$_4$ and 50 μL for TXB$_2$. Samples are then incubated with antibody and tracer in 96 well microtiter plates (which are pre-coated with 5 μg mouse anti-rabbit IgG antibody per well) at room temperature overnight. After washing off excess antibody and tracer, 200 μL of Ellman's reagent (Immunoassay kit, Cayman Chemical Company) are added to the well, and samples are incubated at 25° C. for 4 hours. OD at 405 nm is measured. Inhibitors, the calcium ionophore A23187, and test compounds are dissolved in DMSO as stock solutions (10 mM) and added to the assays at various concentrations in a total volume of 10 μL. The effect of A87689 in this assay is reported in Table 4.

TABLE 4

Activity of A87689 in PLA$_2$ In Vitro Assays

| Assay | IC$_{50}$ Calcium salt | IC$_{50}$ Free Acid. |
|---|---|---|
| Snake venom (Naja naja) PLA$_2$ | 8.0 μg/mL | 6.3 μg/mL |
| Purified human cytosolic PLA$_2$ | 22 μg/mL | 17.2 μg/mL |
| Whole cell HL-60 cell assay | inactive | * |

*The free acid has some activity at 10 μM, but inhibitory activity plateaus at 30–40% inhibition.

TABLE 5

Activity of A87689 Compounds
in the Snake Venom (Naja naja)
PLA$_2$ Assay

| Compound | IC$_{50}$ |
|---|---|
| Free Acid | 6.3 µg/mL |
| Tetra-acetate Calcium Salt | 9.5 µg/mL |
| Penta-Sodium Salt | 6.7 µg/mL |

A87689 in In Vivo Arthritis Models

A87689 was tested in three different in vivo arthritis models designed to test for antiinflammatory activity. In each of these animal models, the hind paw of a rat is injected with a substance which induces an arthritic-like state in the paw joints which is evidenced by the presence of swollen, inflamed soft tissue and bone damage. This state is a form of induced arthritis so that agents which have antiinflammatory activities can be identified through the reduction in inflammation of the tissue and reduction in bone damage.

Test compound was administered orally and by intraperitoneal and subcutaneous injection. Preferably, oral administration is used; however, parenteral dosing of A87689 resulted in excellent antiinflammatory activity. Intraperitoneal injection of many irritant materials often results in peritonitis. Such peritonitis is correlated with antiinflammatory activity as evidenced by reduction in soft-tissue inflammation. In addition, subcutaneous injection of irritant materials may also result in nonspecific antiinflammatory activity. Each experiment was run in parallel with nonspecific irritant controls, such as 1% carrageenin or dilute acetic acid, in order to note how much antiinflammatory activity was nonspecific.

Lipoidalamine-Induced Arthritis Model

The lipoidalamine-induced arthritis test is a model of systemic inflammation and arthritis induced by the adjuvant substance N,N-dioctadecyl-N',N'-bis(2-hydroxyethyl)propanediamine (LA) suspended in mineral oil. The disease that results is very similar to that occurring in Freund's complete adjuvant (FCA) treated rats according to Chang [Chang, Y. Pearson, C. M., and Abe, C., "Adjuvant polyarthritis IV. Induction by a synthetic adjuvant: immunologic, histopathologic, and other studies," *Arth. Rheum.* 23: 62–71, (1980)]. Inflammation occurs in many tissues but is most striking in the spleen and joints. Compounds are tested for their ability to modulate splenic and joint inflammation in established disease (treatment starts on day 9).

The animals (Lewis/Sprague Dawley, males, 200–220 grams) are divided into groups of 5 and housed in hanging cages with food and water ad libitum. On day 0 they are injected with 7.5 mg of LA subcutaneously at the base of the tail. On day 9 the animals are weighed and compound administration is started. The compounds are suspended, using a tissue homogenizer, in a 1% CMC solution. The screening dose is 50 mg/kg orally. Compounds are administered once daily for 5 days (days 9–13) with no dosing on day 14. On day 15 the animals are weighed again and hind paw volume measured using a water manometer. The animals are then anesthetized and bled via cardiac puncture. After the animals are euthanize, the spleen is removed and weighed and the hind feet are removed just above the ankle joint and weighed. The individual blood samples are analyzed for fibrinogen. Means and standard errors for all of these parameters are then calculated, and percent differences from the diseased (LA) control are figured. Statistical significance is determined utilizing the Dunnet T calculation on the raw data. The positive control for the LA arthritis test is dexamethasone. Dexamethasone at a dose of 0.1 mg/kg orally will inhibit paw swelling by 80–90% and spleen weight by 90–100%. Effects on fibrinogen are more variable, but it is usually inhibited by 50–70%.

Compounds that show statistical inhibition of paw swelling or spleen weight are rerun at 50 mg/kg; if activity is confirmed, a dose response is run. Compounds may also be tested in the two complete Freund's adjuvant-induced arthritis models in rats discussed infra.

When calcium salt of A87689 was administered subcutaneously at a dosage of 14 mg/kg in DMSO in this test, the swelling of the injected paw was inhibited by 46%.

When the sodium salt of A87689 was solubilized in water and administered subcutaneously at a dosage of 20 mg/kg in this test, it inhibited swelling of paw volume by 30%. Likewise, when the sodium salt A87689 was solubilized in DMSO and administered intraperitoneally at 10 mg/kg, it inhibited paw swelling by 15%. However, when the sodium salt was solubilized in DMSO and administered subcutaneously at 10 mg/kg, it inhibited paw swelling by 65%.

Freund's Complete Adjuvant Induced Polyarthritis

Two of the in vivo models used were based on the subplantar introduction of FCA into the hind paw of rats, and measurement of the resulting inflammation. The A87689 compound was administered by three methods: intraperitoneally (IP), orally, (PO) and subcutaneously (SC). The two models, which are based on the introduction of FCA into the paw of rats, are the "developing test" and the "established test".

In the developing test, male Wistar-Lewis rats weighing 220–240 grams are used for testing (Harlam Sprague Dawley Laboratories). The animals are acclimated to laboratory conditions for seven days prior to use. Animals are provided Purina Lab Chow and water ad libitum, and lights are cycled 12 hours on and off. FCA is prepared by diluting PERRIGEN (adjuvant, Calbiochem) 1:6 with mineral oil, resulting in a final concentration of 0.083%. On day 0 the rats are given a single subplantar injection of 0.1 mL of FCA suspension in the right hind paw. Animals are divided into groups of 5 and weighed. In the developing test, treatment with the test compound is started on day 0. Normal and FCA controls are administered by placebo vehicle. Paw volumes are measured by an electrically amplified aqueous displacement instrument three days a week. The animals are weighed again on day 14, and the treatment dosage is appropriately adjusted. The test is terminated on day 28, at which time the animals are again weighed, paw volumes are measured, and radiographs are made of both hind paws. Injected and uninjected paw volume curves are made, and areas under the curve are calculated. These areas are compared to the FCA control, and a percent inhibition from the FCA control is calculated. Bone damage scores are determined from analysis of the radiographs based upon periostial elevation, joint space narrowing, and deposition of calcium.

In the developing test, when the calcium salt of A87689 was administered orally at 25 mg/kg in a 1% CMC solution, it inhibited paw swelling by 59%. When the calcium salt of A87689 was administered intraperitoneally at 10 mg/kg in DMSO, it inhibited paw swelling by 98%.

When the sodium salt of A87689 was administered intraperitoneally in DMSO at 5 mg/kg inhibited paw swelling by 108%; however, peritonitis was evident in the rats receiving this treatment. Under the same conditions, but administered at 10 mg/kg, the sodium salt of A87689 inhibited paw swelling by 101% (two rats of this group died from peritonitis).

The "established test" is a variation of the "developing test" in which the all of the conditions are the same but treatments with compound are not started until day 14 or 15 when the rats have an established disease as indicated by at least 0.5 mL of swelling of the uninjected paw.

In the established test, A87689 calcium salt, when administered at 50 mg/kg in 1% CMC intraperitoneally, inhibited the paw swelling of the established lesion by 58%.

EXAMPLE 1

Fermentation of A87689

A. Shake-flask

The culture A87689, NRRL 18815, either as a lyophilized pellet or as a suspension maintained in liquid nitrogen, is used to inoculate a vegetative medium having the composition of vegetative medium A:

| Vegetative Medium A | |
|---|---|
| Ingredient | Amount (%) |
| Glucose | 1.0 |
| Potato Dextrin | 3.0 |
| Soybean Flour | 2.0 |
| Cottonseed flour* | 2.0 |
| CaCO$_3$ | 0.2 |
| Tap H$_2$O | q.s. to 1 liter |

No pH adjustment
*PROFLO Flour, Traders Protein, P.O. Box 8407, Memphis, TN 38108

When the culture is maintained in liquid nitrogen, ampoules are prepared using mycelium from vegetative culture (48 hour incubation, 30° C.) which are suspended to culture volume in suspending medium. The suspending medium contains lactose (100 g), glycerol (200 mL), and deionized water (q.s. to 1 L).

A liquid nitrogen ampoule is used to inoculate 50 mL of vegetative medium in 250 mL flasks. The cultures are incubated at 30° C. for 48 hours on a shaker orbiting in a two-inch (5.08 cm) circle at 250 rpm.

The vegetative culture is used (2% v/v inoculum) to inoculate 50 mL of a production medium having the following composition:

| Production Medium I | |
|---|---|
| Ingredient | Amount (%) |
| Glucose | 3.0 |
| Peptone* | 0.75 |
| Blackstrap Molasses | 0.5 |
| CaCO$_3$ | 0.2 |
| Deionized H$_2$O | q.s. to 1 liter |

No pH adjustment
*BACTO PEPTONE, Difco Laboratories

The inoculated production medium is incubated in 250 mL Erlenmeyer flasks at 30° C. for 5 to 6 days on a shaker orbiting in a two-inch circle at 250 rpm.

B. Stirred Bioreactor Fermentation

In order to provide a larger volume of inoculum, 15 mL of incubated first-stage vegetative culture, prepared as described in Section A, is used to inoculate 600 mL of a second-stage vegetative medium having the same composition as that of the first-stage vegetative medium. The second-stage culture is incubated in a 2-L wide mouth Erlenmeyer flask for about 24 hours at 30° C. on a shaker orbiting in a two-inch circle at 250 rpm.

Incubated second-stage vegetative culture (2.4 L) thus prepared is used to inoculate 80 to 115 liters of sterile production medium II.

| Production Medium II | |
|---|---|
| Ingredient | Amount (%) |
| Glucose | 2.35 |
| Peptone* | 0.75 |
| Blackstrap Molasses | 1.4 |
| CaCO$_3$ | 0.2 |
| Deionized H$_2$O | q.s. to 1 liter |

No pH adjustment; antifoam (SAG 471) is added to the medium to control foam
*BACTO PEPTONE The inoculated production medium is allowed to ferment in a 165-L stirred bioreactor for 7 to 8 days at 30° C. The air flow and agitator speed in the stirred vessel are computer controlled to maintain a dissolved oxygen level at 45% of air saturation. pH is controlled (if needed) between 6.7 and 7.6, using H$_2$SO$_4$ and NaOH. Glucose solution (0.33 g/mL of deionized H$_2$O) is fed at a rate of 4.5 g/L/day starting at 25 to 27 hours after inoculation. The rate is increased to 5.7 g/L/day starting at 42 to 44 hours.

EXAMPLE 2

Fermentation of A87689.1

Compound A87689 is produced according to the method of Example 1, but using the A87689.1 (NRRL 18851) culture.

EXAMPLE 3

Isolation and Purification of A87689

Fermentation broth (88 L) (prepared as described in Example 2) was filtered through a ceramic filter (Membralox Systems, Illinois Wtaer Treatment, Rockford, Ill.) to yield 66 L of filtrate containing A87689. The filtrate was pumped over a stainless steel column (3"×48") of DIAION HP-20SS (a resin of the polystyrene type, Mitsubishi Chemical Industries, Ltd., Tokyo) (5 L) at a flow rate of 500 mL/minute. The column was washed with 20 L of methanol:water (1:3), and the activity was eluted with methanol:water (1:1), collecting 10-4-L fractions. The fractions were assayed for PLA$_2$ inhibitory activity. Fractions 4 and 5, which contained the majority of activity, were combined and concentrated in vacuo to 2500 mL as pool 1. Fractions 3,6,7 and 8 were combined as a second pool of activity. The precipitate which formed in pool 1 was centrifuged off and dissolved in 60 mL DMSO. A 10-mL aliquot of the DMSO solution was pumped onto a DYNAMAX HPLC C$_8$ column (4.1×30 cm) (Rainin Instruments Co., Emeryville, Calif.) containing 400 mL of silica gel C$_8$ (150 A) resin. The column was developed with a gradient of acetonitrile:water:5% NH$_4$OAc (10:85:5) to acetonitrile:water:5% NH$_4$OAc (50:45:5) in 70 minutes with a flow rate of 25 mL/min. and collecting 25 mL fractions. The elution was monitored with a Waters 481 detector (Millipore Corporation, Milford, Mass.) at 254 nm. Crystals which formed in fractions 36, 37, and 38, were filtered off and dried in vacuo. The aliquot separation was repeated 5 more times to give a total yield of 1162 mg of crystalline A87689 salt (decomposed at about 300° C., no true melting point).

EXAMPLE 4

Alternate Procedure for Isolation and Purification of A87689

Whole fermentation broth (225 L), obtained as described in Example 1, was filtered through a filter press with 3% HYFLO SUPERCEL filter aid (diatomaceous earth, Johns Manville Products Corp.). The filtrate (190 L) was adjusted from pH 7.4 to pH 7.0 with 5N HCl; DIAION HP-20 resin (20 L) was added and stirred for 2 hours. The resin was removed by filtration, washed with 100 L of distilled water, then washed with 100 L of water:methanol (3:1) by stirring in a vessel for 30 minutes. The supernate was decanted, and the resin was stirred with 50% aqueous methanol to elute the A87689 activity. The methanol supernate containing the activity was removed by filtration, and the resin was stirred with 100 L of methanol to remove the remainder of the activity and to regenerate the resin. The elution was monitored using the snake venom (*Naja naja*) $PLA_2$ assay.

The 50% methanol eluate was concentrated in vacuo to 20 L; pH was adjusted to 7.0; and the solution was extracted twice with 20 L of n-butanol. The spent aqueous layer was freeze-dried to yield 56 g of crude product. (The purification of this material, which was not n-butanol extractable, is described in Example 4B.) The n-BuOH extracts were combined and concentrated in vacuo to dryness. The residue was dissolved in 100 mL water and 100 mL dioxane and freeze dried to yield 14.7 g of crude A87689. The crude A87689 was dissolved in 300 mL methanol with sonication and allowed to stand at $-10°$ C. until a precipitate formed. The precipitate was filtered off and dried in vacuo to yield 1.4 g of partially purified A87689.

This material (100 mg) was stirred in 10 mL water, and the suspension was adjusted to pH 12.0 with 5N NaOH to dissolve the precipitate. The pH was slowly adjusted to 7.0 with 5N HCl, and the solution was applied to a DYNAMAX 150A column (Rainin Instrument Co., Emeryville, Calif.) containing 100 mL silica gel $C_8$ (150 A) resin. The column was developed with a gradient of acetonitrile:water:1% $NH_4OAc$ (5:85:10) to acetonitrile:water:1% $NH_4OAc$ (50:40:10) in 50 minutes at a flow rate of 8 mL/min. The elution was monitored at 260 nm using a Waters 481 detector (Millipore Corporation, Milford, Mass.). Fractions 2 and 3 were combined, concentrated in vacuo to remove the acetonitrile, and allowed to stand overnight for crystallization. This procedure was repeated, and the crystals from two runs were combined, filtered and dried in vacuo to yield 29 mg of crystalline A87689 calcium salt (m.p.—decomposed above 300° C.). This salt form had a very low solubility in water, but was soluble in DMSO and is called the "water insoluble salt" or the "calcium salt" in discussions of utility.

EXAMPLE 4A

Additional Alternate Procedure for Isolation and Purification of A87689

An alternate procedure to Example 4 was to resuspend the partially purified A87689 dried precipitate in $H_2O$ and apply the solution directly to the column without adjustment from pH 12 to pH 7. The resulting non-crystalline sodium salt was lyophilized and was soluble in water. In discussions of utility, this form is called the "water soluble salt" or the "sodium salt".

EXAMPLE 4B

Purification of the N-Butanol Non-Extractable Preparation

A portion of the n-butanol non-extractable material from Example 4 (200 mg) was dissolved in 10 mL water and applied to a DYNAMAX 150A column containing 100 mL silica gel $C_8$ resin. The column was developed with a gradient of acetonitrile:0.1% $NH_4OAc$ (1:20) to acetonitrile:0.1% $NH_4OAc$ (1:1) in 30 minutes at a flow rate of 10 mL/min, collecting 8-mL fractions and monitoring the elution at 260 nm. Crystals which formed in fraction 22 (the most active fraction) were filtered off and dried in vacuo to yield 8 mg of crystalline A87689 salt. The filtrate was freeze-dried to yield an additional 19 mg of amorphous A87689 salt.

EXAMPLE 5

Preparation of A87689 Free Acid from the A87689 Calcium Salt

Purified A87689 calcium salt (0.44 g), obtained as described in Example 4, was suspended in 5N HCl (0.05 L) at ambient temperature; acetone (0.05 L) was added. A yellow solution was observed after 10 minutes, and after 30 minutes precipitation began. The suspension was stirred 18 hours under nitrogen at ambient temperature. The reaction mixture was reduced to ½ volume in vacuo and filtered to give a yellow powder (0.58 g) after washing with 1N HCl solution. The still wet powder was dissolved in $CHCl_3$ (0.2 L) and washed 2× with $H_2O$. The $CHCl_3$ layer was dried over $Na_2SO_4$. Filtration and removal of the solvent in vacuo gave a yellow foam (0.306 g) which was the free acid of A87689. The final material was yellow and crystalline. TLC (Merck SG) demonstrated 1-spot material ($R_f=0.5$; chloroform:methanol:ammonia, 6:3:1) detected by iodine vapor, and HPLC indicated 77.9% purity. The free acid had an HPLC retention time of 6.4 minutes, using a μBondapak $C_{18}$ SG column (Waters Chromatography Division, Millipore Corporation) in a gradient of $CH_3CN$:0.1% $NH_4OAc$ (1:9 to 7:3) solution at a flow rate of 2 mL/min, and detecting by U.V. at 254 nm.

The free acid of A87689 has the following characteristics:

Molecular weight: 1184.462

Empirical formula: $C_{66}H_{72}O_{20}$

FAB-MS(M+1): Found: 1185.4695: Calculated: 1185.4680

Elemental analysis: Calculated: C, 66.88; H, 6.12 Found: C, 66.52; H, 5.95. No nitrogen or sulfur was detected.

| UV (EtOH, λmax),: | | |
|---|---|---|
| Neutral: | 304 ($\epsilon$ = 54805) | 238 ($\epsilon$ = 64335) |
| Base: | 300 ($\epsilon$ = 56569) | 237 ($\epsilon$ = 72695) |
| Acid: | 314 ($\epsilon$ = 59871) | 236 ($\epsilon$ = 38628) |
|  | 218 ($\epsilon$ = 40085) | |

Melting point: Starts charring >200° to 320° C.

Titration shows pKa of 3.5 (approximately three groups)

Figure 2:
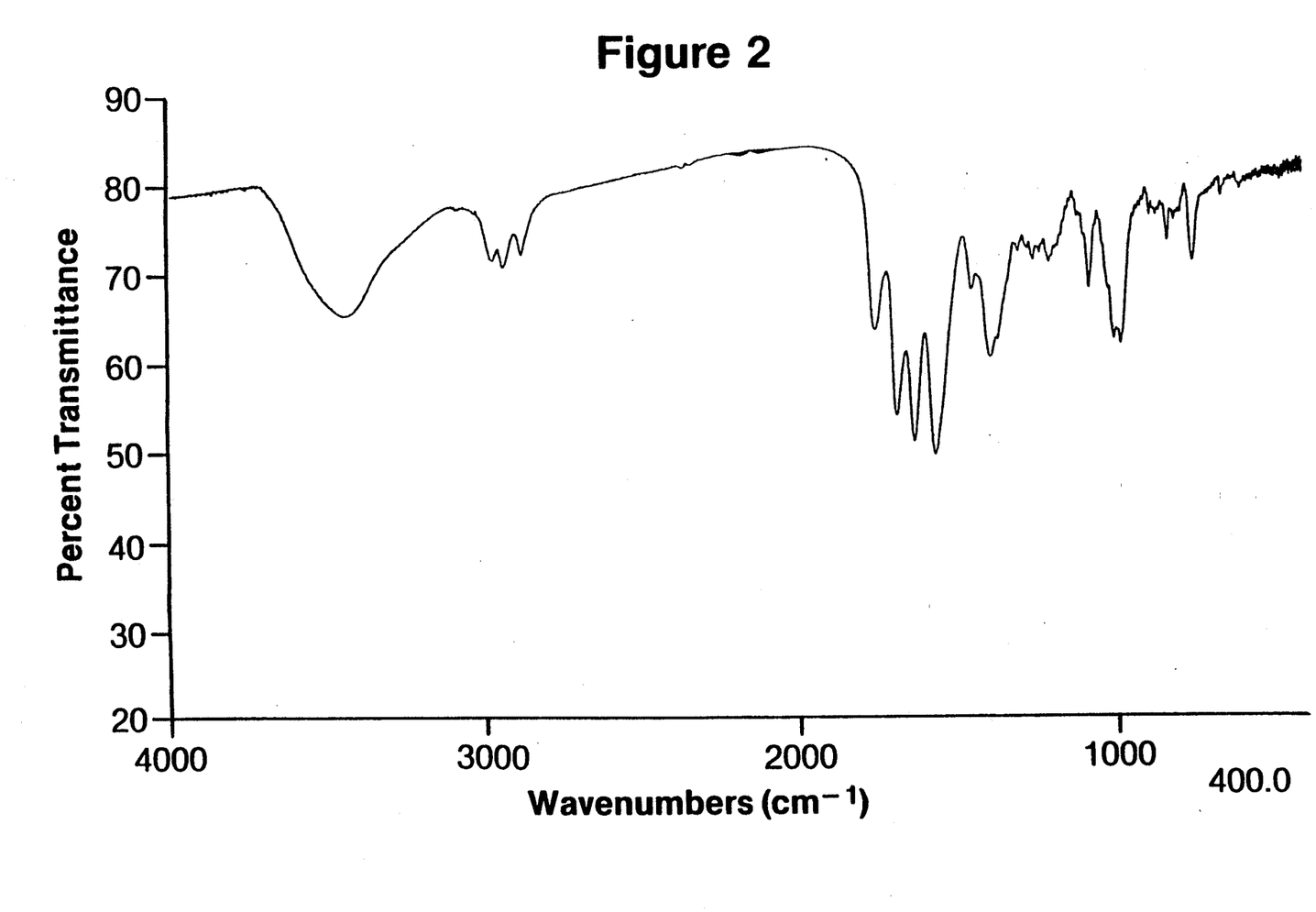
FIG. 2—A87689 free acid.

The IR spectrum of the free acid of A87689 (KBr pellet) is shown in FIG. 2 of the accompanying drawings. The most significant absorption maxima occur at the following frequencies (cm$^{-1}$): 3439, 1758, 1688, 1636, 1568, 1395, 1002, 981 and 753.

EXAMPLE 6

Preparation of the Tetra-acetate Calcium Salt

A87689 calcium salt (100 mg) was dissolved in anhydrous pyridine (3 mL). Acetic anhydride (1 mL) was added to this solution. The solution was heated to 40° C. for 120 hours under nitrogen. The solution was cooled to room temperature, and concentrated to dryness in vacuo to give a tacky residue. The residue was triturated with chloroform: methanol (1:1), filtered, and dried in vacuo to yield a light yellow powder (112 mg). The A87689 tetra-acetate calcium salt had a retention time of 12.2 min. on the HPLC system described in Example 5. The tetra-acetate calcium salt has the following characteristics:

Molecular weight: 1390.460
Empirical formula: $C_{74}H_{78}O_{24}Ca$
FAB-MS(M+1): Found: 1391.4659; Calculated: 1391.4677

| UV (EtOH, λmax): | | |
| --- | --- | --- |
| Neutral: | 300 ($\epsilon$ = 31700) | 238 ($\epsilon$ = 32700) |
| Base: | 295 ($\epsilon$ = 57900) | 206 ($\epsilon$ = 311000) |
| Acid: | 306 ($\epsilon$ = 53900) | 225 (E = 62300) |

Figure 3:
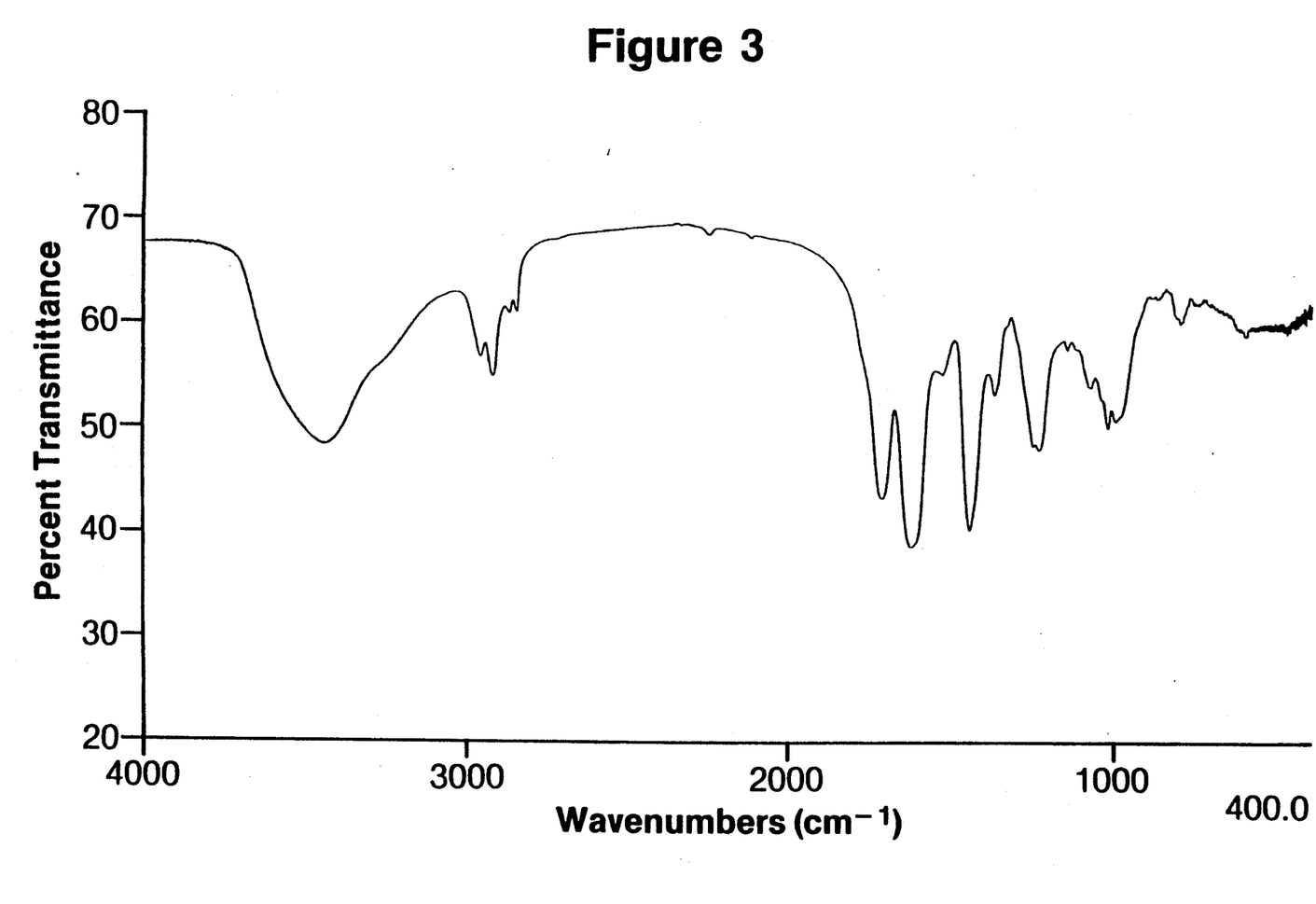
FIG. 3—A87689 tetraacetate calcium salt.

The IR spectrum of the tetra-acetate calcium salt of A87689 (KBr pellet) is shown in FIG. 3 of the accompanying drawings. The most significant absorption maxima occur at the following frequencies (cm$^{-1}$): 3436, 1728, 1641, 1457, 1241, 1027, and 1003.

EXAMPLE 7

Preparation of the A87689 Tetramethyl Ether Calcium Salt

A87689 calcium salt (0.1 g) was dissolved in DMSO (10 mL) containing 10% NaOH (1.5 mL). To this solution, methyl iodide (0.5 mL) was added. This solution was stirred at 40° C. for 18 hours under nitrogen. It was cooled to room temperature and adjusted to pH 1.5 with 1N HCl. The precipitate was collected by filtration, washed 2× with H$_2$O, and dried in vacuo to give 115 mg of tan powder.

The A87689 tetramethyl ether calcium salt had an R$_f$ value of 0.75 on the TLC system described in Example 5. The A87689 tetramethyl ether calcium salt has the following additional characteristics:

Molecular weight: 1280
Empirical formula: $C_{70}H_{78}O_{20}Ca$

Figure 4:
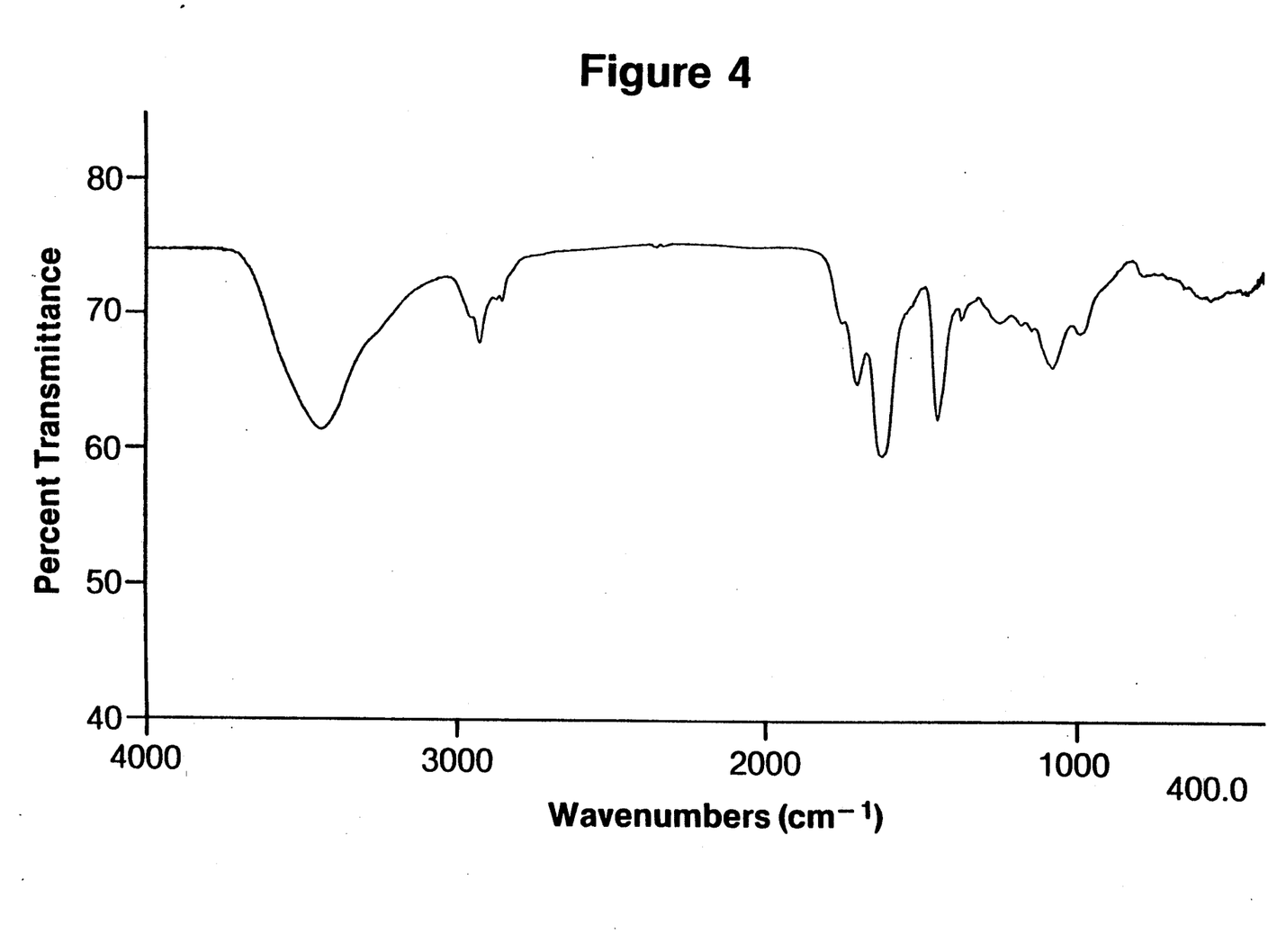
FIG. 4—A87689 tetramethyl ether calcium salt.

The IR spectrum of the tetramethyl ether calcium salt of A87689 (KBr) pellet is shown in FIG. 4 of the accompanying drawings. The most significant absorption maxima occur at the following frequencies (cm$^{-1}$): 3434, 1718, 1637, 1465 and 1089.

EXAMPLE 8

Preparation of the A87689 Penta-Sodium Salt

A87689 free acid (70 mg) was dissolved in MeOH (1 mL), to which was added 1 mL of H$_2$O, followed by an adjustment of the pH to 12 with 2N NaOH. This solution was stirred for one hour at room temperature under nitrogen. The solution was concentrated in vacuo to near dryness to give semi-solids, which were triturated with 2 mL of acetonitrile:methanol (1:1) and filtered to give a white powder (52 mg). This water-soluble powder was triturated with methanol, and the resulting solids were collected and dried to give a white solid (38 mg).

The A87689 penta-sodium salt had an R$_f$ value of 0.3 on the TLC system described in Example 5 and a retention time of 5.25 on the HPLC system described in Example 5. The A87689 penta-sodium salt has the following additional characteristics:

Molecular weight: 1294.371
Empirical formula: $C_{66}H_{67}O_{20}Na_5$
FAB-MS(M+1): Found: 1295.3814 Calculated: 1295.3792

| UV (EtOH, λmax) | | |
| --- | --- | --- |
| Neutral: | 299 ($\epsilon$ = 40379) | 237 ($\epsilon$ = 47771) |
| Base: | 299 ($\epsilon$ = 42623) | 235 ($\epsilon$ = 30162) |
| Acid: | 312 ($\epsilon$ = 40908) | 235 ($\epsilon$ = 30162) |
|  | 221 ($\epsilon$ = 29110) | |

Figure 5:
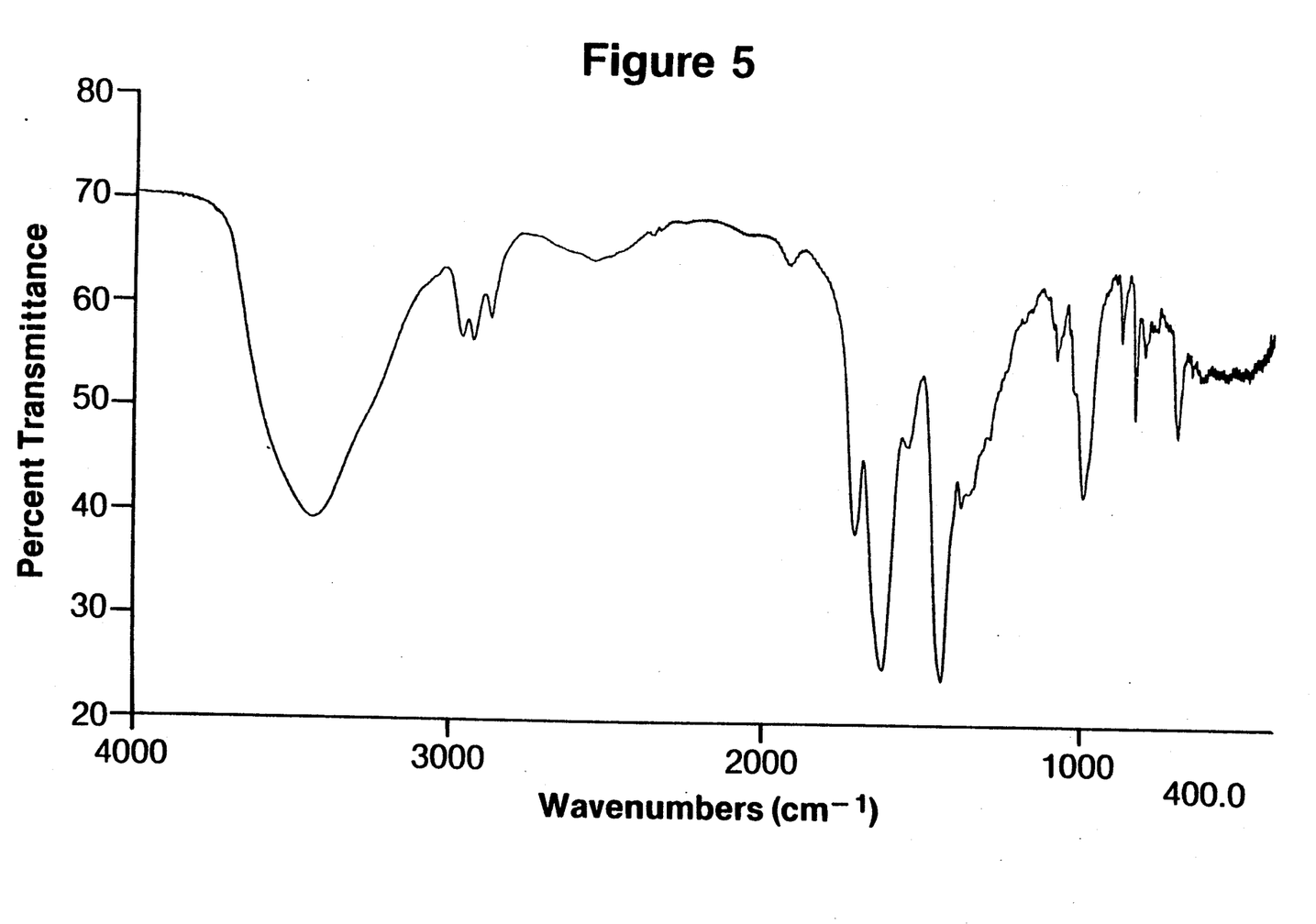
FIG. 5—A87689 penta-sodium salt.

The IR spectrum of the penta-sodium salt of A87689 (KBr pellet) is shown in FIG. 5 of the accompanying drawings. The most significant absorption maxima occur at the following frequencies (cm$^{-1}$): 3430, 1710, 1623, 1436, 996, 834 and 701.

EXAMPLE 9

Preparation of the A87689 Tetramethyl Ether Free Acid

A87689 calcium salt (50 mg) was dissolved in 5 mL DMSO containing 0.8 mL of 10% NaOH solution. To this was added 0.25 mL methyl iodide. This reaction was stirred at 40° C. for 18 hours under nitrogen. The reaction was then cooled to room temperature, and the pH was adjusted to 2 with 5N HCl. The reaction mixture was then concentrated to 0.75 the original volume under vacuum and diluted with 100 mL CHCl$_3$. The CHCl$_3$ layer was washed 2× with 5% Na$_2$S$_2$O$_3$ followed by 2 washes with water. The organic layer was removed and dried under vacuum to yield 68 mg creamy-yellow solids. The solids were triturated with petroleum ether B and then with diethyl ether. The solids were collected by filtration and dried under vacuum to yield 33 mg of a fine yellow residue.

The A87689 tetramethyl ether free acid had an R$_f$ value of 0.7 on the TLC system described in Example 5 and a retention time of 10.23 minutes on the HPLC system described in Example 5. The A87689 tetramethyl ether free acid has the following additional characteristics:

Molecular Weight: 1240
Empirical formula: $C_{70}H_{80}O_{20}$
FAB-MS(M+1): Found: 1241.5387 Calculated: 1241.5322

| UV (EtOH, λmax) | | |
| --- | --- | --- |
| Neutral: | 304 ($\epsilon$ = 47104) | 239 ($\epsilon$ = 51704) |
| Base: | 296 ($\epsilon$ = 51763) | 233 ($\epsilon$ = 71752) |
|  | 212 ($\epsilon$ = 227629) | |
| Acid: | 312 ($\epsilon$ = 50737) | 233 ($\epsilon$ = 37297) |
|  | 218 ($\epsilon$ = 37705) | |

We claim:

1. A biologically purified culture of *Amycolatopsis mediterranei* selected from the group consisting of NRRL 18815, NRRL 1851, and mutants of said cultures which produce A87689 compounds.

2. A culture of claim 1 which is *A. mediterranei* NRRL 18815 or mutants of said culture which produces A87689 compounds.

3. A culture of claim 1 which is *A. mediterranei* NRRL 18851 or mutants of said culture which produces A87689 compounds.

* * * * *

UNITED STATES PATENT AND TRADEMARK OFFICE
CERTIFICATE OF CORRECTION

PATENT NO. : 5,278,064
DATED : January 11, 1994
INVENTOR(S) : Dennis R. Berry, et al It is certified that error appears in the above-indentified patent and that said Letters Patent is hereby corrected as shown below:

On the title page:

Inventors "Dennis R. Berry, Greenwood; Anne D. Dantzig, Crawfordsville; Manuel Debono, Indianapolis; Robert Hamil, Greenwood; R. Michael Molloy, Danville; Raymond C. Yao, Carmel..." should read --Anne H. Dantzig, Crawfordsville; Robert Hamil, Greenwood; Raymond C. Yao, Carmel...--

Signed and Sealed this

Twenty-third Day of August, 1994

Attest:

BRUCE LEHMAN

*Attesting Officer*   *Commissioner of Patents and Trademarks*